US005411865A

United States Patent [19]

Reed

[11] Patent Number: 5,411,865

[45] Date of Patent: May 2, 1995

[54] METHOD OF DETECTING ANTI-LEISHMANIA PARASITE ANTIBODIES

[75] Inventor: Steven Reed, Bellevue, Wash.

[73] Assignee: Iasys Corporation, Seattle, Wash.

[21] Appl. No.: 6,676

[22] Filed: Jan. 15, 1993

[51] Int. Cl.[6] .......................................... G01N 33/569

[52] U.S. Cl. ................................. 435/7.22; 435/7.92; 435/7.95; 435/975; 530/324; 530/822; 530/810

[58] Field of Search .................... 435/7.22, 7.92, 7.95, 435/975, 973, 970, 6; 530/324, 388.6, 822, 810, 812; 430/518, 528, 804, 808, 811

[56] References Cited

PUBLICATIONS

Burns et al, "Molecular Characterization of a kinesin-related antigen of *Leishmania chagasi* that detects specific antibody in African and American visceral leishmaniasis," Proc. Natl. Acad. Sci. USA, 90(2): 775-779 (Jan. 15, 1993).

Zhang et al, "Use of a Recombinant 170-Kilodalton Surface Antigen of *Entamoeba histolytica* for Serodiagnosis of Amebiasis and Identification of Immunodominant Domains of the Native Molecule", J. Clin. Microbiol., 30(11):2788-2792 (Nov. 1992).

*Primary Examiner*—Carol E. Bidwell

*Attorney, Agent, or Firm*—Patricia Anne Perkins; Scott G. Hallquist; Christopher L. Wight

[57] ABSTRACT

A method for detecting anti-Leishmania parasite antibodies to a 230 kDa antigen present in *Leishmania chagasi* and *Leishmania donovani* is disclosed which comprises obtaining a sample from an individual, contacting the sample with a recombinant K39 repeat unit antigen comprising the amino acid sequence as shown in SEQ ID NO:3, and detecting the presence of anti-Leishmania parasite antibodies in the sample which bind to the recombinant K39 repeat unit antigen.

7 Claims, 6 Drawing Sheets

METHOD OF DETECTING ANTI-LEISHMANIA PARASITE ANTIBODIES

TECHNICAL FIELD OF THE INVENTION

The present invention provides a method for diagnosing leishmaniasis in a patient suspected of being infected with the parasitic protozoa Leishmania. The present invention further provides a diagnostic kit for use in diagnosing Leishmania, and an antigen useful for diagnosing the presence of Leishmania and as a vaccine to prevent infection with Leishmania.

BACKGROUND OF THE INVENTION

The transmission of pathogenic Leishmania involves an injection of extracellular promastigotes into a mammalian host by an infected sandfly. The promastigotes rapidly attach and enter monocytes and cells of the reticuloendothelial system, where they transform into amastigotes and multiply within phagolysosomes. Analysis of the interaction of Leishmania promastigotes with the target host cell suggests that both parasite and host molecules are involved in cell adhesion. Clinical symptoms of leishmaniasis range from self-healing skin lesions to diffuse cutaneous and mucosal manifestations, or severe visceral involvement of the spleen, liver and lymph nodes (visceral leishmaniasis or VL).

Visceral leishmaniasis is generally caused by *Leishmania donovani* in Africa and India, *L. infantum* in Southern Europe or *L. chagasi* in Latin America. In VL, high levels of parasite specific antibodies are observed prior to detection of antigen specific T cell responses (Ghose et al., *Clin. Exp. Immunol.* 40:318–326, 1980). This antibody response has been exploited for serodiagnosis of infection with *L. chagasi* and *L. donovani.* The current World Health Organization's estimate of 12 million cases of leishmaniasis and recent epidemics of visceral leishmaniasis in Sudan and India highlight the need for more effective early diagnosis and therapeutic agents. Also at least 400,000 new cases of VL are diagnosed annually. The current diagnostic tests to measure an antibody response use whole or lysed parasites. Therefore, there is a need in the art to improve the diagnostic accuracy for diagnosing VL early while the potentially fatal disease is more treatable.

Recovery from leishmaniasis correlates with the development of specific T lymphocyte responses and usually confers long-lasting immunity against reinfection (Carvalho et al., *J. Clin. Invest.* 76:2066–6, 1985 and Carvalho et al., *J. Immunol.* 135:4144–8, 1985). Both recovery from disease and resistance to reinfection are dependent on the development of specific T lymphocyte responses. Interferon gamma (IFN-γ) is a product of activated T cells, has demonstrated anti-leishmania activity in vitro (Murray et al., *J. Clin. Invest.* 72:1506, 1983 and Nacy et al., *J. Immunol.* 135:1305, 1985), and in vivo (Reed et al., *J. Immunol.* 132:3116, 1984 and Murray. et al., *J. Immunol.* 1348:2290, 1987) and has been used effectively in the clinical treatment of leishmaniasis (Harms et al., *Lancet* 10:1287, 1989 and Badaro et al., *N. Engl. J. Med.* 322:16, 1990).

One antigen, called gp63, has been cloned (Miller et al., *Mol. Biochem. Parasitol.* 38, 267–274, 1990) and was found to be a metalloprotease and is highly conserved among different species of Leishmania (Etges et al., *J. Biol. Chem.* 261:9098, 1986; Chaudhuri et al., *Mol. Biochem. Parasitol.* 27:43, 1988; Chaudhuri et al., *J. Biol. Chem.* 264:7483, 1989; Colmer-Gould et al., *J. Exp. Med.* 162:902, 1985; and Button et al., *J. Exp. Med.* 167:724, 1988). Gp63 is relatively abundant on both the infective promastigote stage and the intracellular amastigote stage (Frommel et al., *Mol. Biochem. Parasitol.* 38:25–32, 1990 and Medina-Acosta et al., *Mol. Biochem. Parasitol.* 37:263, 1989). Gp63 is important for both parasite entry into macrophages (Russel and Wilheim, *J. Immunol.* 136:2613, 1986; Chang et al., *Proc. Natl. Acad. Sci. USA* 83:100, 1986; Wilson and Hardin, *J. Immunol.* 141:265, 1988; and Mosser and Edelson *J. Immunol.* 135:2785, 1985) and subsequent survival within the phagosome (Chaudhuri et al., *J. Biol. Chem.* 264:7483, 1989). Immunization with native gp63 in vivo partially protected susceptible mice against cutaneous disease (Handman and Mitchell *Proc. Natl. Acad. Sci. USA* 82:5910, 1985 and Russel and Alexander *J. Immunol.* 140:1274, 1988). Moreover, recombinant gp63 expressed in Salmonella conferred partial protection by oral immunization against *Leishmania major* infection in resistant mice (Yang et al., *J. Immunol.* 145:2281, 1990). Both native gp63 and recombinant gp63 elicited strong proliferative responses, as well as IFN-γ production, from leishmaniasis patients with a spectrum of clinical disease (Russo et al., *J. Immunol.* 147:3575, 1991).

SUMMARY OF THE INVENTION

The present invention provides a method for diagnosing leishmaniasis comprising: (a) obtaining a sample from a patient suspected of being infected with a Leishmania parasite, wherein the sample contains antibodies from the patient; and (b) determining the presence of antibodies that bind to a K39 repeat unit antigen from the sample. Preferably the inventive method is a serodiagnostic method utilizing sera from the individual suspected of harboring a Leishmania parasite. Preferably the antigen used is one or a plurality of K39 repeat sequences, wherein the K39 repeat sequence comprises the amino acid sequence (in single letter designation) L E Q Q L R (D/E) S E (E/A) R A A E L A S Q L E (A/S) T (A/T) A A K (M/S) S A E Q D R E (N/S) T R A (T/A) or (in three letter designation) Leu Glu Gln Gln Leu Arg (Asp/Glu) Ser Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) (SEQ ID NO:3). Preferably, the inventive method further comprises the step of determining the presence of antibodies that bind to a native or recombinant gp63 polypeptide.

The present invention further provides a diagnostic kit for evaluating a patient antibody-containing sample for the presence of anti-Leishmania parasite antibodies, comprising a K39 repeat unit antigen. Preferably, the K39 repeat unit antigen is bound to a solid phase. Preferably, the diagnostic kit further comprises an anti-human antibody conjugated to a detection moiety. Preferably the antigen used is one or a plurality of K39-repeat sequences, wherein the K39 repeat sequence comprises the amino acid sequence Leu Glu Gln Gln Leu Arg (Asp/Glu) Ser Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) (SEQ ID NO:3). Most preferably, the diagnostic kit further comprises a gp63 polypeptide, in combination with a K39 repeat unit antigen.

BRIEF DESCRIPTION OF THE DRAWINGS AND SEQUENCES

FIG. 1 shows the expression and purification of recombinant K39 (rK39) antigen. The gels shows Coomassie blue-stained 12% SDS-polyacrylamide gel of molecular weight markers (lane 1), *E. coli* lysates from uninduced cells (lane 2), and induced cultures (lane 3) of clone K39, and purified rK39 (lane 4, 2 μg).

FIG. 2 shows reactivity of patient sera with rK39. Blots containing *L. chagasi* promastigote lysate (lane 1, 10 μg), purified rK39 (lane 2, 50 ng) and *T. cruzi* epimastigote lysate (lane 3, 10 μg) were probed with individual *L. chagasi* VL sera (A–C), individual *L. donovani* VL sera (D–F), or pooled mucosal leishmaniasis (G, n=4), cutaneous leishmaniasis (H, n-4), or *T. cruzi* infection (I, n=5) sera. Pooled normal human sera (n=3) and no primary antibody controls are shown (J and K, respectively). Bound antibody was detected with $^{251}$I-protein A.

FIGS. 3A and 3B show a Southern blot analysis of the LcKin gene sequences. Genomic DNA (2.5 μg/lane) from *L. chagasi* digested with Bam HI (lane 1), Hind III (lane 2) and Pst I (lane 3) or Pst I digested DNA from *L. amazonesis* (lane 4), *L. braziliensis* (lane 5), *L. guyanesis* (lane 6), *L. donovani* (lane 7), *L. infantum* (lane 8), *L. major* (lane 9), or *T. cruzi* (lane 10) were analyzed by Southern blotting. The blots were probed (FIG. 3A) with a 2.4 kb Hind III fragment from the LcKin homology domain or (FIG. 3B) with the 915 bp repetitive insert of K39.

FIGS. 4A, 4B and 4C show reactivity of rabbit anti-rK39 antiserum on recombinant and native leishmania lysates. FIG. 4A is an immunoblot of purified rK39 (50 ng per lane) transferred from 12% SDS-polyacrylamide gels and probed with preimmune rabbit serum (lane 1) or rabbit anti-rK39 (lane 2). FIG. 4B is an immunoblot of *L. chagasi* promastigote (lanes 1 and 5, 10 μg) and amastigote (lanes 2 and 6 10 μg) lysates or *L. amazonensis* promastigote (lanes 3 and 7, 10 μg) and amastigote (lanes 4 and 8, 10 μg) lysates, transferred from 7.5% SDS-polyacrylamide gels and probed with preimmune rabbit serum (lanes 1–4) or rabbit anti-rK39 (lanes 5–8). FIG. 4C is an immunoblot showing reactivity of rabbit antisera raised against *L. chagasi* ribosomal protein PO, described in Skeiky et al. (*J. Exp. Med.* 176:201, 1992), with lanes 1–4 of FIG. 4B.

FIGS. 5A and 5B show an ELISA evaluation of patient seroreactivity on *L. chagasi* promastigote lysate (panel A) or purified rK39 (panel B). Absorbance values (mean+SEM) of Brazilian VL (VL-B, n=57), Sudanese VL (VL-S, n=52), *T. cruzi* infection (Tc, n=35), Brazilian cutaneous leishmaniasis (CL-B, n=13), Sudanese cutaneous leishmaniasis (CL-S, n=13) mucosal leishmaniasis (ML, n=15) and normal (n=15) sera.

FIG. 6 shows patient sera reactivities against recombinant gp63. All sera samples were diluted 1:100 and assayed by an ELISA technique. Individual absorbance values are represented by dots; horizontal and vertical bars represent the mean ±95% confidence limit (Student's t-test), respectively. The abbreviations are visceral leishmaniasis (VL), cutaneous leishmaniasis (CL), and mucosal leishmaniasis (MCL).

SEQ ID NO:1 is the amino acid sequence for K39.

SEQ ID NO:2 is the DNA sequence encoding a K39 polypeptide.

SEQ ID NO:3 is the amino acid sequence of a 39 amino acid repeat unit antigen.

DETAILED DESCRIPTION OF THE INVENTION

The present invention provides a method for diagnosing VL and a diagnostic kit for VL. The present invention was made possible by the discovery of a K39 gene and its DNA sequence and deduced amino acid sequence having a plurality of antigenic 39 amino acid repeat units. The K39 gene was found in an attempt to characterize leishmania antigens recognized by a spectrum of VL patients, including VL patients infected with either *L. donovani* or *L. chagasi.*

Figure 1:
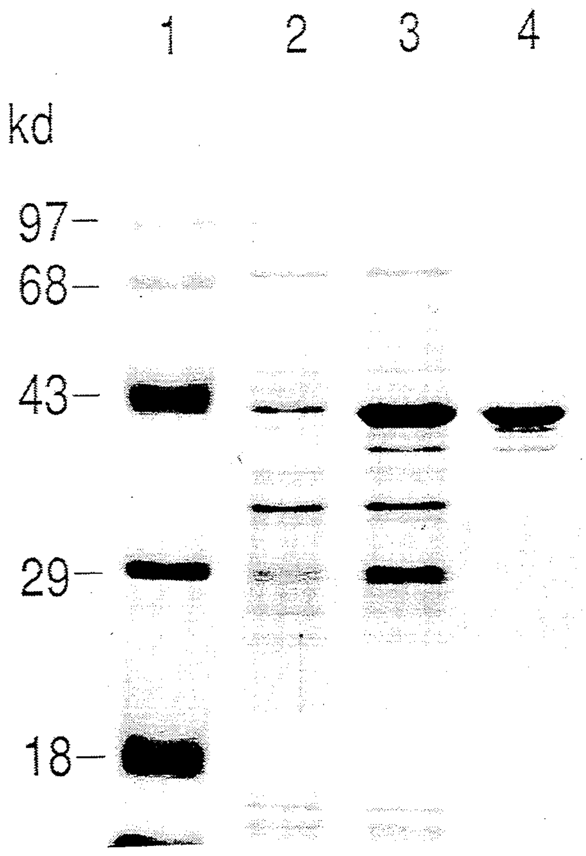

A *L. chagasi* genomic DNA expression library was screened with sera obtained from a patient having VL caused by *L. donovani.* From approximately 32,000 recombinants screened, seven clones were selected based upon reactivity with this patient's sera. The seven clones contained inserts ranging from 0.9 kb to 2.6 kb and expressed immunoreactive recombinant proteins of 35 kDa to 100 kDa. Clone K39 was exceptionally reactive with the test serum. Recombinant K39 antigen (rK39) migrated on Coomassie-stained SDS-PAGE as a 39 kDa protein in induced bacterial extracts (FIG. 1, lane 3). The protein was purified by ammonium sulfate fractionation and preparative isoelectric focusing (FIG. 1, lane 4) with a yield of 25–30 mg per liter.

The DNA and deduced amino acid sequences of the insert of clone K39 were determined and are provided in SEQ ID NO's 1 and 2 herein. The DNA sequence contained a single open reading frame encoding 298 amino acids with a predicted molecular weight of 32.7 kDa and a pI of 4.4. Recombinant clone K39 contains an additional 6.2 kDa of plasmid fusion sequences. In this sequence was noted 6.5 copies of a randomly arrayed 39 amino acid repeat sequence. SEQ ID NO:3 shows the consensus sequence of the repeat unit.

To further characterize this gene, clones containing sequences flanking the K39 gene fragment were isolated from the *L. chagasi* library using a K39 insert probe. Sequence analysis of one overlapping clone, LcKin, showed that the open reading frame extended for 1971 base pairs in the 5' direction, encoding 657 nonrepetitive amino acids. 5' to the putative ATG initiation codon, 454 base pairs of sequence were obtained with multiple termination codons in each reading frame. Partial characterization of clones containing 3' flanking sequences indicated that the repeat domain extended for approximately 3 to 4 kb.

GenPept and Swiss-Protein data bank searches revealed similarity between LcKin and several members of the superfamily of kinesin-related proteins, particularly in the N-terminal motor domain. A relatively high level of sequence conservation was observed in the putative ATP and microtubule binding domains (Yang et al., *Cell* 56:879, 1989). The remaining 500 residues showed little similarity to sequence of the tail regions of kinesin and myosin of a number of species. Secondary structure analysis predicted that this portion of LcKin (amino acids 426–955) contain greater than 90% helical structure, a feature characteristic of a coil-coiled tail regions of several motor proteins. Therefore, the repetitive epitope of the rK39 antigen appears to be present in *L. chagasi* as part of the tail region of a leishmania kinesin-related protein.

The present invention provides an identification of a 230 kDa antigen of *L. chagasi,* LcKin, with sequence homology to the kinesin superfamily of motor proteins. The gene is predominantly expressed by tissue amastigotes. The DNA sequence is present in at least seven diverse species of Leishmania. The DNA sequence further comprises an extensive repetitive domain containing a 39 amino acid repeat unit. Southern analysis showed the repeat unit of LcKin to be variable among species, but was closely related in *L. chagasi* and *L. donovani*. Most significantly, there are high antibody titers in 98% of Brazilian VL patients to rK39, a recombinant antigen containing 6.46 copies of the 39 amino acid repeat sequence. Similar antibody levels were detected in 100% of tested Sudanese VL patients. These data indicate conservation of the repeat sequence between *L. chagasi* and *L. donovani*.

The present cloning of LcKin represents the first characterization of a gene encoding a protozoan motor protein. These microtuble based motors are involved in such varied intracellular processes as organelle and synaptic vescicle transport, chromosome segregation and spindle pole separation, nuclear fusion, protein sorting a flagellar beating. This tail domain is usually characterized by a predominantly alpha-helical structure which likely forms a coil interacting with different intracellular ligands which determine its function. The LcKin gene product is similar to members of this family in primary sequence, particularly in the putative ATP and microtubule binding domains, as well as in predicted secondary structure.

The inventive feature of LcKin was the high prevalence of antibody specific to the rK39 repeat sequence in VL patients from geographically distinct endemic regions of Brazil and the Sudan. Therefore, the rK39 repeat antigen is useful as a vaccine and as an antibody-binding antigen for a diagnostic kit for the detection and diagnosis of VL. Moreover, the inventive method for diagnosing VL using rK39 was specific for VL patients. False positives were not seen in normal patients, even normal patients from the endemic areas of Brazil and the Sudan. These data also reflect relatedness among members of the *L. donovani* complex. The data described herein provide a thorough analysis of patient antibody responses to a purified recombinant antigen (rK39) of *L. chagasi* and show a marked restriction of this response to *L. chagasi* and *L. donovani* infected patients with VL with 98% and 100% positivity in this group. The inventive diagnostic kit and the inventive method for diagnosing VL and distinguishing VL from other infectious diseases with similar clinical presentations provides a needed tool in a clinicians hands in endemic areas of the world. Therefore, antibody reactivity to rK39 is an improved replacement for promastigote-based serological tests for the diagnosis of acute VL.

The rK39 antigen is an immunodominant B cell epitope comprising one or more copies of the Leu Glu Gln Gln Leu Arg (Asp/Glu) Set Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) (SEQ ID NO:3) 39 amino acid repeat sequence. Preferably the K39 antigen comprises from 1 to about 7 copies of the 39 amino acid sequence. Most preferably, the K39 antigen comprises about 6 copies of this sequence.

Gp63 is a major surface glycoprotein of Leishmania parasites, is highly conserved among species and is expressed in both infective and intracellular stages. The gp63 gene of *L. chagasi* has been cloned, analyzed and described in Miller et al. (*Mol. Biochem. Parasitol.* 39:276, 1990). It is significant to note that the sequence of *L. chagasi* was found to differ significantly from that published for *L. major* (Button et al. *J. Exp. Med.* 167:724, 1988). The predicted protein sequences of gp63 from *L. major* and *L. chagasi* are closely related. Gp63 is a surface metalloprotease (Bouvier et al., *Mol Biochem. Parasitol.* 37:235, 1989 and Medina-Acosta et al., *Mol Biochem. Parasitol.* 37:263, 1989) that is also important for parasite entry into macrophages and survival within the phagosome. Native gp63 (ngp63) and recombinant gp63 (rgp63) elicited strong proliferative responses and IFN-$\gamma$ production from leishmaniasis patients with a spectrum of clinical disease. The present invention further found the prevalence of gp63-specific antibodies among patients with clinically and geographically diverse leishmaniasis to provide a further useful diagnostic tool alone or in combination with the use of the K39 antigen for diagnosis of VL.

Figure 6:
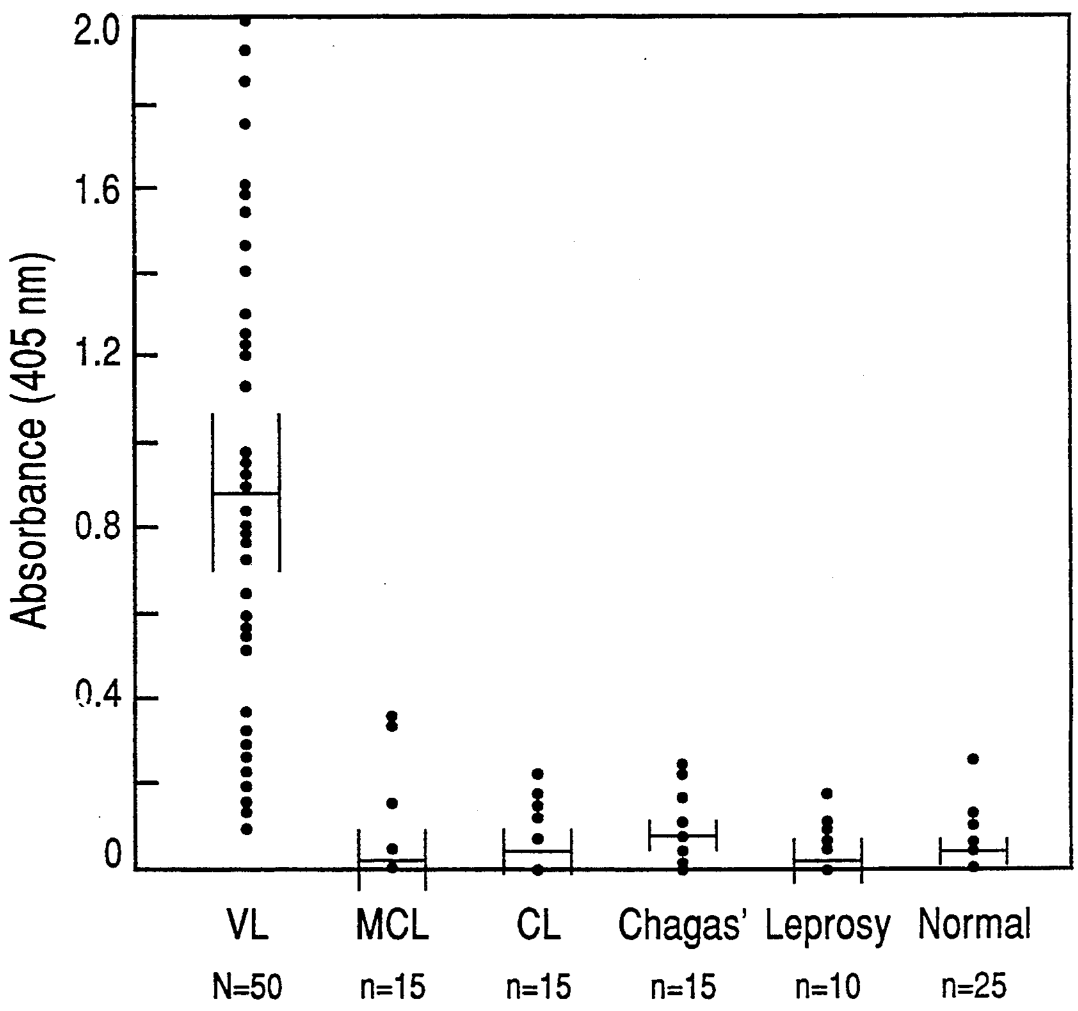

The prevalence of gp63-specific antibody among leishmaniasis and other disease groups was examined by an ELISA technique (described in Example 4 herein). All leishmaniasis sera were obtained from patients with active disease, and included Brazilian visceral, cutaneous or mucosal leishmaniasis from a study area in Bahia, Brazil or from biopsy-positive patients in the Sudan. Leprosy sera were from patients in Haiti where leishmaniasis has not been reported. Normal control sera were from normal volunteers in the U.S. FIG. 6 shows that there were elevated anti-gp63 antibody levels among VL patients (mean absorbance=0.89). In fact, 84% (42/50) of the VL patient sera tested have absorbance values greater than 3 standard deviations above the mean of normal control sera. The remaining 16% had relatively low levels of gp63-specific antibody, despite generally high titers of leishmania-specific antibody (mean absorbance value of 1.54). In contrast, cutaneous and mucosal leishmaniasis patients showed very little sero-reactivity with only two mucosal patients having absorbance values significantly above control normals. No sera samples from patients with a *T. cruzi* infection or leprosy showed significantly elevated antibody levels to rgp63. These results indicate that gp63 is a potent B cell immunogen among VL patients although alone is not as good of an antigen in a diagnostic assay as is K39. However, the combination antigens of K39 and gp63 can provide a superior diagnostic kit with a reduced number of false positive results.

EXAMPLE 1

This example illustrates the cloning of the K39 antigen. A genomic library was constructed with mechanically sheared DNA of *L. chagasi* (MHOM/BR/82/BA-2,C1) in the expression vector lambda ZAPII according to the manufacturer's protocols (Stratagene, La Jolla, Calif.). Recombinants were screened with serum (obtained from a patient recently treated for acute *L. donovani* infection) preadsorbed to remove anti-*E. coli* reactivity according to the procedure described in Sambrook et al. *Molecular Cloning, A Laboratory Manual,* 2nd Ed. (Cold Spring Harbor, N.Y., 1989).

The K39 clone was expressed to produce rK39 polypeptide and this was purified from a 25% to 40% ammonium sulfate fraction of a soluble bacterial lysate by preparative isoelectric focusing with a Bio-Rad Rotofor IEF cell and 1% 3/10 ampholytes (Bio-Rad, Richmond, Calif.) in the presence of 8M urea and 10 mM dithiothreitol. Peak fractions were concentrated by a second ammonium sulfate precipitation, and dialyzed against 25 mM Tris-HCl (pH 8), 150 mM NaCl (TBS). Protein concentrations were determined using a Pierce BCA protein assay (Pierce, Rockford, Ill.) and purity assessed by Coomassie-blue staining following SDS-PAGE.

A radiolabeled insert of K39 was used to screen the *L. chagasi* genomic library to obtain clones containing sequences flanking the K39 gene fragment. A set of overlapping deletions of clones K39 and LcKin were generated by controlled Exonuclease III digestion (according to the procedure described in Henikoff, Gene 28:351, 1984) to obtain a complete sequence of both the coding and noncoding strands. Single stranded template was prepared as described in Burns et al. (*Proc. Natl. Acad. Sci. USA* 89: 1239, 1992) and nucleotide sequence was obtained by the Sanger dideoxynucleotide chain termination method using $^{35}$S-labeled dATP (Sanger et al., *Proc. Natl. Acad. Sci. USA* 74:5463, 1977) or by fluorescence-based sequencing on an Applied Biosystems Sequencer Model 373A, according to the manufacturer's protocols. Sequence comparisons were made with GenPept (72.0) and Swiss-Prot (22.0) with the Lipman/Pearson method (Pearson and Lipman, *Proc. Natl. Acad. Sci. USA* 85:2444, 1988). Secondary structural predictions were made according to Garner et at. (*J. Mol. Biol.* 120:97, 1978) and Chou et al. (*Advances in Enzymology* 47:45, 1978).

DNA from *Leishmania spp.* and *T. cruzi* (MHOM/CH/00/Tulahuen C2) were isolated, digested with Pst I, separated by agarose gel electrophoresis, and analyzed by Southern blotting. The blots were probed with a 2.4 kb Hind III fragment of LcKin derived from the 5′ end of the gene (probe A) or a 915 bp insert of clone K39 (probe B). Each probe was radiolabeled with $\alpha$-$^{32}$P (dCTP) to a specific activity of $9\times10^8$ cpm/$\mu$g using random oligonucleotides as primers (Boehinger Manheim, Indianapolis). The final washes were for 1 hr in 0.1× SSC/0.5% SDS at 68° C. Blots of *L. chagasi* DNA digested with Bam HI, Hind III and Pst I and no Hind III restriction sites were used and probed as above to assess gene copy. Probe A contained one Bam HI, one Pst I, and no Hind III restriction sites. Probe B did not contain sites for these restriction enzymes.

Figures 3A, 3B:
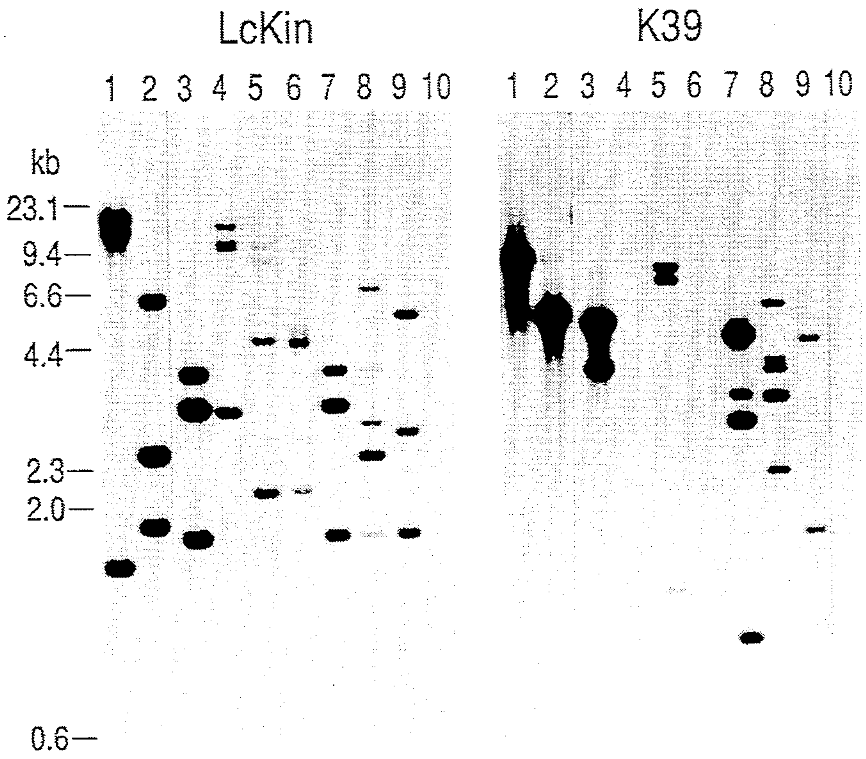

FIG. 3A shows the blot of probe A and FIG. 3B shows the blot of probe B. Probe A hybridized strongly to multiple Pst I restriction fragments of all *Leishmania spp.* tested (FIG. 3A, lanes 3–9), indicating conservation in the kinesin homology domain. Polymorphism in size and number of hybridizing restriction sites were noted. Less conservation in the repetitive domain of the LcKin gene was observed as probe B hybridized with varying intensity to Pst I restriction fragments of *L. chagasi* (MHOM/BR/82/BA-2,C1), *L. amazonensis* (IFLA/BR/67/PH8), *L. braziliensis* (MHOM/BR/75/M2903, obtained from Dr. Diane McMahon-Pratt, Yale University, New Haven, Conn.), *L. donovani* (MHOM/Et/67/HU3), *L. infantum* (IPT-1, obtained from Dr. Lee Schnur, Hebrew University-Hadassah Medical School, Jerusalem, Israel), and *L. major* (LTM p-2, obtained from Dr. David Moser, Temple Univ. Phila, Pa.), but not *L. guyanesis* (MHOM/BR/75/M4147) (FIG. 3B, lanes 3–9). Given the intensity of the hybridization signals, the K39 repeat sequence appeared to be most closely related between *L. chagasi* and *L. donovani* (FIG. 3B, lanes 3 and 7). No hybridization with either probe was observed with *T. cruzi* DNA (FIG. 3, lane 10).

Using *L. chagasi* digested DNA, two Pst I fragments were detected with probe B, indicating the presence of a second copy of the LcKin gene or polymorphism in restriction sites present in the 3′ repetitive sequences (FIG. 3B, lane 3). Probe A hybridized to three fragments in each of the Bam HI, Hind III, and Pst I digests of *L. chagasi* DNA (FIG. 3A, lanes 1–3). Taken together, the Southern blot data show that the LcKin gene is present in a minimum of 2–3 copies in the *L. chagasi* genome, and that related sequences are present in the seven species of Leishmania examined.

EXAMPLE 2

This example illustrates the identification of native LcKin antigen. Rabbit anti-rK39 serum was used to probe SDS-PAGE blots of *L. chagasi* promastigote and tissue amastigote lysates to partially characterize native LcKin protein. Promastigotes were cultured in axenic media. Tissue amastigotes were obtained from spleens of Syrian hamsters or footpads of Balb/c ByJ mice and purified as described in Burns et al. (*J. Immunol.* 146:742, 1991). Rabbit anti-rK39 serum was obtained by subcutaneous immunization of an adult New Zealand white rabbit (R & R Rabbitry, Stanwood, Wash.) with 200 $\mu$g of purified rK39 administered in Freund's incomplete adjuvant (IFA Gibco, Grand Island, N.Y.) together with 100 mg of N-acetylmuramyl-L-alanyl-D-isoglutamine (muramyl dipeptide, Calbiochem, San Diego, Calif.). Five weeks later, the rabbit was boosted with 200 $\mu$g rK39 in IFA alone. Four weeks later, the rabbit was boosted intravenously with 25 $\mu$g of purified rK39. The rabbit serum was collected 6 days later.

Figure 4A:
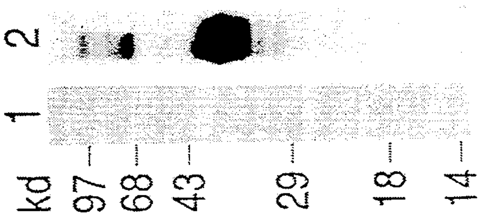
Figure 4B:
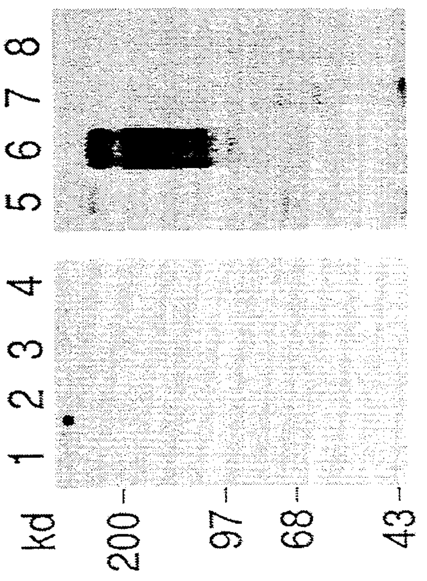
Figure 4C:
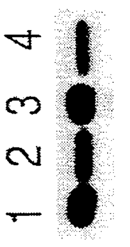

The antiserum bound specifically to purified rK39 (FIG. 4A, lane 2) and to an approximately 230 kDa antigen present in amastigotes (FIG. 4B, lane 6) and to a lesser degree in promastigotes (FIG. 4B, lane 5). No reactivity with this serum was detected in promastigote and amastigote lysates of *L. amazonensis* (FIG. 4B, lanes 7–8) indicative of the variability within this repeat. Comparable amounts of lysate were loaded in all lanes as shown by reactivity of a rabbit anitserum raised against a constitutively expressed *L. chagasi* ribosomal phosphoprotein, Lc P0 (Skeiky et al., *J. Exp. Med.* 176:201, 1992) (FIG. 4C, inset). No reactivity was apparent in pre-immune serum (FIG. 4A, lane 1, FIG. 4B lanes 1–4).

EXAMPLE 3

Figure 2:

This example illustrates the reactivity of patient sera to recognize the rK39 antigen. Patient sera were obtained from well characterized Brazilian visceral, cutaneous and mucosal patients as well as *T. cruzi* infection sera from a study area in Bahia, Brazil. African visceral and cutaneous leishmaniasis sera were from biopsy-positive patients in the Sudan. Normal sera were from clinically healthy individuals living in endemic areas of the Sudan or from the U.S. The sera were analyzed by an immunoblot assay. Immunoblots of parasite lysates or purified rK39 were prepared as described in Burns et al. (*J. Immunol.* 146:742, 1991). Filters were blocked with TBS containing 5% non-fat dried milk and probed with patient sera (1:250) or rabbit sera (1:400) diluted with TBS with 0.1% Tween-20 and 1% bovine serum albumin. Bound antibody was detected with $^{125}$I-labeled Protein A ($1\times10^6$ cpm/blot) followed by autoradiography. Both rK39 and *L. chagasi* promastigote lysates were strongly recognized by *L. chagasi* (FIG. 2A–C) and *L. donovani* (FIG. 2D–F) infection sera. Reactivity with rK39 was not observed with pools of sera obtained from mucosal (FIG. 2G) or cutaneous (FIG. 2H) leishmaniasis patient sera or with a pool of Chagas' disease (e.g., *T. cruzi*) patient sera (FIG. 2I). The pools of sera obtained from mucosal or cutaneous leishmaniasis Chagas' disease patient sera reacted strongly with promastigote lysates. These data indicate that the K39 antigen is specific to *L. chagasi* and *L. donovani* and/or K39 induces a strong antibody response only in VL patients.

EXAMPLE 4

This example illustrates reactivity of patient sera with rK39 as determined by an ELISA. The patient sera were obtained as described in Example 3. The ELISA was conducted by diluting rK39 or *L. chagasi* promastigote lysate in coating buffer (15 mM $Na_2HCO_3$, 28 mM $NaH_2CO_3$. pH 9.6) to 1 μg/ml or 20 μg/ml, respectively. Microassay plates (Probind, Falcon, Lincoln Park, N.J.) were sensitized with rK39 (50 ng) or promastigote lysate (1 μg/ml) by overnight incubation at 4° C. Plates were blocked with PBS plus 1% Tween-20 for 1 hr at room temperature. After five washes with PBS containing 0.1% Tween-20 (PBS-T), 50 μl per well of sera diluted 1:100 with PBS-T were incubated for 30 min at room temperature. The wells were again washed five times with PBS-T and bound antibody was detected by Protein A-HRP (Zymed, So San Francisco, Calif.) as described in Reed et al. (*Am. J. Trop. Med. Hyg.* 43:632, 1990). Absorbance values are relative to the mean of five control sera assayed on each plate. ELISA values of at least three standard deviations greater than the mean absorbance of the normal control sera were considered positive.

Figure 5A:
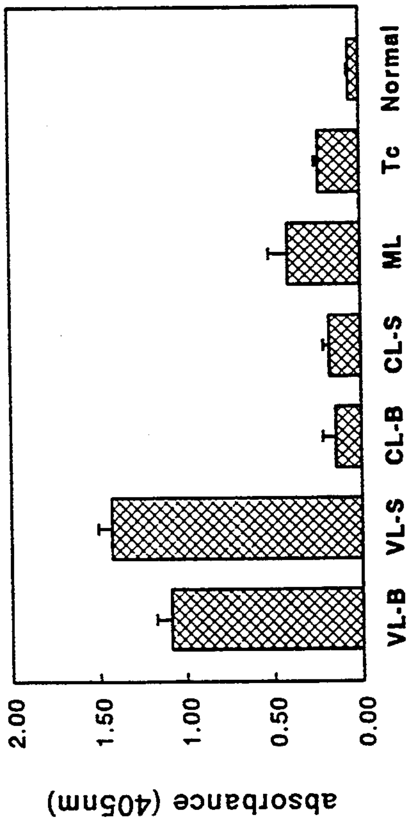
Figure 5B:
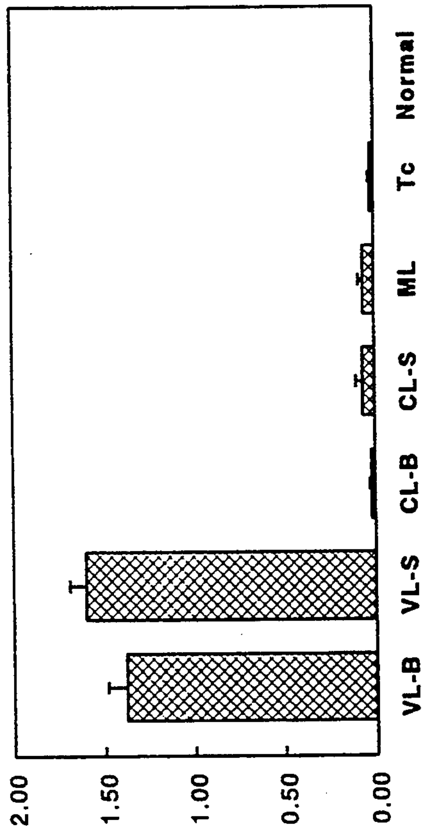

I observed a high level of reactivity among VL patients with 98.2% (56 of 57) of Brazilian VL sera and 100% (52 of 52) of Sudanese VL sera exhibiting positive absorbance values. The positive absorbance values ranged from 0.05 to >2.0 (mean=1.38) among Brazilian VL sera (FIG. 5A) and from 0.094 to >2.0 (mean=1.60) among Sudanese sera (FIG. 5B). Detectable antibody to rK39 was restricted to VL patients, as little or no anti-rK39 response was observed in sera from mucosal or cutaneous leishmaniasis patients or *T. cruzi* infection sera, despite some reactivity in these latter samples with crude *L. chagasi* lysate (FIG. 5).

EXAMPLE 5

This example illustrates a method for producing and purifying recombinant gp63 (rgp63). Recombinant gp63 from *L. chagasi* and *L. donovani* was produced in *E. coli* as a non-fusion protein using T7 RNA polymerase expression system and pET plasmid expression vectors as described in Button et al. (*Mol. Biochem. Parasitol.* 44:213, 1991). Induced bacterial pellets were resuspended in lysis buffer (LB, 50 mM Tris HCl, pH 8.0, 100 mM NaCl, 10 mM EDTA) and lysed by treatment with lysozyme and sonication. The inclusion body fraction containing rgp63 was recovered by centrifugation for 5 min at 200×g and washed twice in LB with 4M urea as a chaotropic agent. The final pellet containing rgp63 was solubilized in 100 mM Tris, pH 8.5, containing 8M urea and 100 mM dithiotretiol. Following dialysis, rgp63 was isolated by ammonium sulfate fractionation, followed by preparative isoelectric focusing in the presence of 8M urea with 3/10 ampholytes using a Rotofor IEF cell (Bio-Rad, Richmond, Calif.) as described in Reed et al. (*Am. J. Trop. Med. Hyg.* 44:272, 1991). Protein concentrations of rgp63 were determined using the Pierce BCA protein assay (Pierce, Rockford, Ill.) and purity assessed by silver-staining (Bio-Rad) after SDS-PAGE as described in Laemmli (*Nature* 227:680, 1970).

I claim:

1. A method for detecting anti-Leishmania parasite antibodies to a 230 kDa antigen present in *Leishmania chagasi* and *Leishmania donovani,* comprising:

(a) obtaining a sample from an individual;

(b) contacting the sample from the individual with a recombinant K39 repeat unit antigen comprising the amino acid sequence Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa (SEQ ID NO:3), wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala; and (c) detecting the presence of anti-Leishmania parasite antibodies in the sample which bind to the recombinant K39 repeat unit antigen.

2. The method of claim 1 wherein the sample is a blood sample.

3. The method of claim 1 wherein the recombinant K39 repeat unit antigen is a plurality of K39 repeat sequences, wherein the K39 repeat sequence comprises the amino acid sequence Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa (SEQ ID NO:3), wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala.

4. A kit for evaluating an antibody-containing sample for the presence of anti-Leishmania parasite antibodies to a 230 kDa antigen present in *Leishmania chagasi* and *Leishmania donovani,* comprising:

a recombinant K39 repeat unit antigen comprising the amino acid sequence Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa (SEQ ID NO:3), wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala; and a detection reagent for detecting the anti-Leishmania parasite antibodies.

5. The kit of claim 4, wherein the K39 repeat unit antigen is bound to a solid phase.

6. The kit of claim 4 wherein the detection reagent is an anti-human antibody conjugated to a detection moiety.

7. The kit of claim 4, wherein the recombinant K39 repeat unit antigen is a plurality of K39 repeat sequences, wherein the K39 repeat sequence comprises the amino acid sequence Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa (SEQ ID NO:3), wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 955 amino acids
( B ) TYPE: amino acid
( D ) TOPOLOGY: linear ( i i ) MOLECULE TYPE: protein ( i x ) SEQUENCE DESCRIPTION: SEQ ID NO: 1:

| | | | | | | | | | | | | | | |
|---|---|---|---|---|---|---|---|---|---|---|---|---|---|---|
| Met | His | Pro | Ser | Thr | Val | Arg | Arg | Glu | Ala | Glu | Arg | Val | Lys | Val |
| 1 | | | | 5 | | | | | 10 | | | | | 15 |
| Ser | Val | Arg | Val | Arg | Pro | Leu | Asn | Glu | Arg | Glu | Asn | Asn | Ala | Pro |
| | | | | 20 | | | | | 25 | | | | | 30 |
| Glu | Gly | Thr | Lys | Val | Thr | Val | Ala | Ala | Lys | Gln | Ala | Ala | Ala | Val |
| | | | | 35 | | | | | 40 | | | | | 45 |
| Val | Thr | Val | Lys | Val | Leu | Gly | Gly | Ser | Asn | Asn | Ser | Gly | Ala | Ala |
| | | | | 50 | | | | | 55 | | | | | 60 |
| Glu | Ser | Met | Gly | Thr | Ala | Arg | Arg | Val | Ala | Gln | Asp | Phe | Gln | Phe |
| | | | | 65 | | | | | 70 | | | | | 75 |
| Asp | His | Val | Phe | Trp | Ser | Val | Glu | Thr | Pro | Asp | Ala | Cys | Gly | Ala |
| | | | | 80 | | | | | 85 | | | | | 90 |

-continued

| | | | | | | | | | | | | | | |
|---|---|---|---|---|---|---|---|---|---|---|---|---|---|---|
| Thr | Pro | Ala | Thr | Gln | Ala | Asp | Val | Phe | Arg | Thr | Ile | Gly | Tyr | Pro |
| | | | | 95 | | | | | 100 | | | | | 105 |
| Leu | Val | Gln | His | Ala | Phe | Asp | Gly | Phe | Asn | Ser | Cys | Leu | Phe | Ala |
| | | | | 110 | | | | | 115 | | | | | 120 |
| Tyr | Gly | Gln | Thr | Gly | Ser | Gly | Lys | Thr | Tyr | Thr | Met | Met | Gly | Ala |
| | | | | 125 | | | | | 130 | | | | | 135 |
| Asp | Val | Ser | Ala | Leu | Ser | Gly | Glu | Gly | Asn | Gly | Val | Thr | Pro | Arg |
| | | | | 140 | | | | | 145 | | | | | 150 |
| Ile | Cys | Leu | Glu | Ile | Phe | Ala | Arg | Lys | Ala | Ser | Val | Glu | Ala | Gln |
| | | | | 155 | | | | | 160 | | | | | 165 |
| Gly | His | Ser | Arg | Trp | Ile | Val | Glu | Leu | Gly | Tyr | Val | Glu | Val | Tyr |
| | | | | 170 | | | | | 175 | | | | | 180 |
| Asn | Glu | Arg | Val | Ser | Asp | Leu | Leu | Gly | Lys | Arg | Lys | Lys | Gly | Val |
| | | | | 185 | | | | | 190 | | | | | 195 |
| Lys | Gly | Gly | Gly | Glu | Glu | Val | Tyr | Val | Asp | Val | Arg | Glu | His | Pro |
| | | | | 200 | | | | | 205 | | | | | 210 |
| Ser | Arg | Gly | Val | Phe | Leu | Glu | Gly | Gln | Arg | Leu | Val | Glu | Val | Gly |
| | | | | 215 | | | | | 220 | | | | | 225 |
| Ser | Leu | Asp | Asp | Val | Val | Arg | Leu | Ile | Glu | Ile | Gly | Asn | Gly | Val |
| | | | | 230 | | | | | 235 | | | | | 240 |
| Arg | His | Thr | Ala | Ser | Thr | Lys | Met | Asn | Asp | Arg | Ser | Ser | Arg | Ser |
| | | | | 245 | | | | | 250 | | | | | 255 |
| His | Ala | Ile | Ile | Met | Leu | Leu | Leu | Arg | Glu | Glu | Arg | Thr | Met | Thr |
| | | | | 260 | | | | | 265 | | | | | 270 |
| Thr | Lys | Ser | Gly | Glu | Thr | Ile | Arg | Thr | Ala | Gly | Lys | Ser | Ser | Arg |
| | | | | 275 | | | | | 280 | | | | | 285 |
| Met | Asn | Leu | Val | Asp | Leu | Ala | Gly | Ser | Glu | Arg | Val | Ala | Gln | Ser |
| | | | | 290 | | | | | 295 | | | | | 300 |
| Gln | Val | Glu | Gly | Gln | Gln | Phe | Lys | Glu | Ala | Thr | His | Ile | Asn | Leu |
| | | | | 305 | | | | | 310 | | | | | 315 |
| Ser | Leu | Thr | Thr | Leu | Gly | Arg | Val | Ile | Asp | Val | Leu | Ala | Asp | Met |
| | | | | 320 | | | | | 325 | | | | | 330 |
| Ala | Thr | Lys | Gly | Ala | Lys | Ala | Gln | Tyr | Ser | Val | Ala | Pro | Phe | Arg |
| | | | | 335 | | | | | 340 | | | | | 345 |
| Asp | Ser | Lys | Leu | Thr | Phe | Ile | Leu | Lys | Asp | Ser | Leu | Gly | Gly | Asn |
| | | | | 350 | | | | | 355 | | | | | 360 |
| Ser | Lys | Thr | Phe | Met | Ile | Ala | Thr | Val | Ser | Pro | Ser | Ala | Leu | Asn |
| | | | | 365 | | | | | 370 | | | | | 375 |
| Tyr | Glu | Glu | Thr | Leu | Ser | Thr | Leu | Arg | Tyr | Ala | Ser | Arg | Ala | Arg |
| | | | | 380 | | | | | 385 | | | | | 390 |
| Asp | Ile | Val | Asn | Val | Ala | Gln | Val | Asn | Glu | Asp | Pro | Arg | Ala | Arg |
| | | | | 395 | | | | | 400 | | | | | 405 |
| Arg | Ile | Arg | Glu | Leu | Glu | Glu | Gln | Met | Glu | Asp | Met | Arg | Gln | Ala |
| | | | | 410 | | | | | 415 | | | | | 420 |
| Met | Ala | Gly | Gly | Asp | Pro | Ala | Tyr | Val | Ser | Glu | Leu | Lys | Lys | Lys |
| | | | | 425 | | | | | 430 | | | | | 435 |
| Leu | Ala | Leu | Leu | Glu | Ser | Glu | Ala | Gln | Lys | Arg | Ala | Ala | Asp | Leu |
| | | | | 440 | | | | | 445 | | | | | 450 |
| Gln | Ala | Leu | Glu | Arg | Glu | Arg | Glu | His | Asn | Gln | Val | Gln | Glu | Arg |
| | | | | 455 | | | | | 460 | | | | | 465 |
| Leu | Leu | Arg | Ala | Thr | Glu | Ala | Glu | Lys | Ser | Glu | Leu | Glu | Ser | Arg |
| | | | | 470 | | | | | 475 | | | | | 480 |
| Ala | Ala | Ala | Leu | Gln | Glu | Glu | Met | Thr | Ala | Thr | Arg | Arg | Gln | Ala |
| | | | | 485 | | | | | 490 | | | | | 495 |
| Asp | Lys | Met | Gln | Ala | Leu | Asn | Leu | Arg | Leu | Lys | Glu | Glu | Gln | Ala |

-continued 500 505 510

Arg Lys Glu Arg Glu Leu Leu Lys Glu Met Ala Lys Lys Asp Ala
515 520 525

Ala Leu Ser Lys Val Arg Arg Arg Lys Asp Ala Glu Ile Ala Ser
530 535 540

Glu Arg Glu Lys Leu Glu Ser Thr Val Ala Gln Leu Glu Arg Glu
545 550 555

Gln Arg Glu Arg Glu Val Ala Leu Asp Ala Leu Gln Thr His Gln
560 565 570

Arg Lys Leu Gln Glu Ala Leu Glu Ser Ser Glu Arg Thr Ala Ala
575 580 585

Glu Arg Asp Gln Leu Leu Gln Gln Leu Thr Glu Leu Gln Ser Glu
590 595 600

Arg Thr Gln Leu Ser Gln Val Val Thr Asp Arg Glu Arg Leu Thr
605 610 615

Arg Asp Leu Gln Arg Ile Gln Tyr Glu Tyr Gly Glu Thr Glu Leu
620 625 630

Ala Arg Asp Val Ala Leu Cys Ala Ala Gln Glu Met Glu Ala Arg
635 640 645

Tyr His Ala Ala Val Phe His Leu Gln Thr Leu Leu Glu Leu Ala
650 655 660

Thr Glu Trp Glu Asp Ala Leu Arg Glu Arg Ala Leu Ala Glu Arg
665 670 675

Asp Glu Ala Ala Ala Ala Glu Leu Asp Ala Ala Ala Ser Thr Ser
680 685 690

Gln Asn Ala Arg Glu Ser Ala Cys Glu Arg Leu Thr Ser Leu Glu
695 700 705

Gln Gln Leu Arg Glu Ser Glu Glu Arg Ala Ala Glu Leu Ala Ser
710 715 720

Gln Leu Glu Ala Thr Ala Ala Ala Lys Ser Ser Ala Glu Gln Asp
725 730 735

Arg Glu Asn Thr Arg Ala Thr Leu Glu Gln Gln Leu Arg Glu Ser
740 745 750

Glu Ala Arg Ala Ala Glu Leu Ala Ser Gln Leu Glu Ala Thr Ala
755 760 765

Ala Ala Lys Met Ser Ala Glu Gln Asp Arg Glu Asn Thr Arg Ala
770 775 780

Thr Leu Glu Gln Gln Leu Arg Asp Ser Glu Glu Arg Ala Ala Glu
785 790 795

Leu Ala Ser Gln Leu Glu Ser Thr Thr Ala Ala Lys Met Ser Ala
800 805 810

Glu Gln Asp Arg Glu Ser Thr Arg Ala Thr Leu Glu Gln Gln Leu
815 820 825

Arg Asp Ser Glu Glu Arg Ala Ala Glu Leu Ala Ser Gln Leu Glu
830 835 840

Ser Thr Thr Ala Ala Lys Met Ser Ala Glu Gln Asp Arg Glu Ser
845 850 855

Thr Arg Ala Thr Leu Glu Gln Gln Leu Arg Glu Ser Glu Glu Arg
860 865 870

Ala Ala Glu Leu Ala Ser Gln Leu Glu Ser Thr Thr Ala Ala Lys
875 880 885

Met Ser Ala Glu Gln Asp Arg Glu Ser Thr Arg Ala Thr Leu Glu
890 895 900

Gln Gln Leu Arg Asp Ser Glu Glu Arg Ala Ala Glu Leu Ala Ser
905 910 915

-continued

```
Gln Leu Glu Ala Thr Ala Ala Ala Lys Ser Ser Ala Glu Gln Asp
                920                 925                 930

Arg Glu Asn Thr Arg Ala Ala Leu Glu Gln Gln Leu Arg Asp Ser
                935                 940                 945

Glu Glu Arg Ala Ala Glu Leu Ala Ser Gln
                950                 955
```

( 2 ) INFORMATION FOR SEQ ID NO: 2:

( i ) SEQUENCE CHARACTERISTICS:
( A ) LENGTH: 3319 base pairs
( B ) TYPE: nucleic acid
( C ) STRANDEDNESS: single
( D ) TOPOLOGY: linear ( i i ) MOLECULE TYPE: cDNA to mRNA ( i i i ) ORIGINAL SOURCE:
( A ) ORGANISM: Leishmania chagasi ( i x ) SEQUENCE DESCRIPTION: SEQ ID NO: 2:

```
GCTCCCACGG CGCTACCCCC TTTCCCGCAT GTGCGACAGT TTCACGCGTAC 51
AAACGTCTTT CTCTCTCCTT CGCGCGTGTC GCTATGGGCG GCGGCGCGTC 101
GGTGTCTTTG ATTGCACAGC TCACCGCCTC GCCATATTTT CGTCGTGGCC 151
ACGCGACCCC CCGACCTTCC CCTCCTCCGC CCCCAAAGAC AAGCCAGACA 201
TACCGACCAT GCCGTCTGCC CGCGTCTCTG CTTACCAAGC GCGCCACGCA 251
CCCCTTCCTC GGCCCTGAAT CTTTCGCGCG GCGCCATACA TTGCATGCAC 301
GTCACTACGC CTGTACACCT TACACCTCCT CTTGCCCACC CCTTTCCCCT 351
TCTACACGCC TAACTACACA CACATATATA TATATATATA TAAAGCGCTC 401
AACGCACACA TACTGTGGCC AGTATTACTG CACCAACGTC TGCCTCTTCC 451
AGGATGCACC CTTCCACTGT GCGGCGTGAG GCGGAGCGGG TGAAGGTGTC 501
GGTGCGCGTG CGCCCCCTAA ACGAACGTGA AAACAATGCC CCGGAAGGGA 551
CGAAAGTGAC CGTTGCGGCG AAACAGGCGG CCGCCGTGGT GACGGTCAAG 601
GTCCTGGGAG GCAGCAACAA CAGCGGCGCC GCCGAGTCGA TGGGGACTGC 651
AAGGCGGGTA GCGCAGGACT TTCAGTTCGA CCACGTGTTC TGGTCTGTGG 701
AGACGCCGGA CGCGTGCGGC GCGACCCCCG CGACGCAGGC AGACGTGTTC 751
CGGACGATCG GGTACCCGCT GGTGCAGCAC GCGTTCGACG GGTTCAACTC 801
GTGCTTGTTT GCGTACGGGC AGACAGGGAG CGGGAAGACG TACACGATGA 851
TGGGCGCGGA CGTGAGCGCG CTTAGTGGTG AGGGCAACGG CGTGACGCCG 901
CGGATCTGCC TGGAGATCTT TGCGCGGAAG GCGAGCGTGG AGGCGCAGGG 951
GCACTCGCGG TGGATCGTGG AGCTGGGGTA CGTGGAGGTG TACAACGAGC 1001
GCGTGTCGGA CCTGCTTGGG AAGCGGAAGA AGGGTGTGAA GGGCGGCGGC 1051
GAGGAGGTGT ACGTGGACGT GCGCGAGCAC CCGAGCCGCG GCGTGTTCCT 1101
GGAGGGGCAG CGGCTGGTGG AGGTTGGGAG CCTGGACGAT GTTGTGCGGC 1151
TGATCGAGAT CGGCAACGGC GTGCGGCACA CCGCTTCGAC GAAGATGAAC 1201
GACCGGAGCA GCCGGAGCCA CGCGATCATC ATGCTGCTGC TGCGCGAGGA 1251
GCGGACGATG ACGACGAAGA GCGGGGAGAC GATCCGTACT GCCGGCAAGA 1301
GCAGCCGCAT GAACCTTGTG GACCTTGCGG GGTCTGAGCG CGTGGCGCAG 1351
TCGCAGGTGG AGGGGCAGCA GTTCAAGGAG GCGACGCACA TCAACCTGTC 1401
```

-continued

```
GCTGACGACG CTCGGGCGCG TGATCGACGT GCTCGCGGAC ATGGCGACGA 1451
AGGGTGCGAA GGCGCAGTAC AGCGTTGCGC CGTTCCGCGA CTCGAAGCTG 1501
ACGTTCATCC TGAAGGACTC GCTTGGCGGG AACTCGAAGA CGTTCATGAT 1551
CGCGACTGTG AGCCCGAGCG CGCTGAACTA CGAGGAGACG CTGAGCACGC 1601
TGCGGTACGC GTCGCGCGCG CGCGACATTG TGAATGTTGC GCAGGTGAAC 1651
GAGGACCCGC GCGCACGGCG GATCCGCGAG CTGGAGGAGC AGATGGAGGA 1701
CATGCGGCAG GCGATGGCTG GCGGCGACCC CGCGTACGTG TCTGAGCTGA 1751
AGAAGAAGCT TGCGCTGCTG GAGTCGGAGG CGCAGAAGCG TGCGGCGGAC 1801
CTGCAGGCGC TGGAGAGGGA GCGGGAGCAC AACCAGGTGC AGGAGCGGCT 1851
GCTGCGCGCG ACGGAGGCGG AGAAGAGCGA GCTGGAGTCG CGTGCGGCTG 1901
CGCTGCAGGA GGAGATGACC GCGACTCGAC GGCAGGCGGA CAAGATGCAG 1951
GCGCTGAACC TGCGGCTGAA GGAAGAGCAG GCGCGCAAGG AGCGCGAGCT 2001
GCTGAAAGAG ATGGCGAAGA AGGACGCCGC GCTCTCGAAG GTTCGGCGAC 2051
GCAAAGACGC CGAGATAGCA AGCGAGCGCG AGAAGCTGGA GTCGACCGTG 2101
GCGCAGCTGG AGCGTGAGCA GCGCGAGCGC GAGGTGGCTC TGGACGCATT 2151
GCAGACGCAC CAGAGAAAGC TGCAGGAAGC GCTCGAGAGC TCTGAGCGGA 2201
CAGCCGCGGA AAGGGACCAG CTGCTGCAGC AGCTAACAGA GCTTCAGTCT 2251
GAGCGTACGC AGCTATCACA GGTTGTGACC GACCGCGAGC GGCTTACACG 2301
CGACTTGCAG CGTATTCAGT ACGAGTACGG GGAAACCGAG CTCGCGCGAG 2351
ACGTGGCGCT GTGCGCCGCG CAGGAGATGG AGGCGCGCTA CCACGCTGCT 2401
GTGTTTCACC TGCAAACGCT CCTGGAGCTC GCAACCGAGT GGGAGGACGC 2451
ACTCCGCGAG CGTGCGCTTG CAGAGCGTGA CGAAGCCGCT GCAGCCGAAC 2501
TTGATGCCGC AGCCTCTACT TCCCAAAACG CACGTGAAAG CGCCTGCGAG 2551
CGGCTAACCA GCCTTGAGCA GCAGCTTCGC GAATCCGAGG AGCGCGCTGC 2601
GGAGCTGGCG AGCCAGCTGG AGGCCACTGC TGCTGCGAAG TCGTCGGCGG 2651
AGCAGGACCG CGAGAACACG AGGGCCACGC TAGAGCAGCA GCTTCGCGAA 2701
TCCGAGGCGC GCGCTGCGGA GCTGGCGAGC CAGCTGGAGG CCACTGCTGC 2751
TGCGAAGATG TCAGCGGAGC AGGACCGCGA GAACACGAGG GCCACGCTAG 2801
AGCAGCAGCT TCGTGACTCC GAGGAGCGCG CTGCGGAGCT GGCGAGCCAG 2851
CTGGAGTCCA CTACTGCTGC GAAGATGTCA GCGGAGCAGG ACCGCGAGAG 2901
CACGAGGGCC ACGCTAGAGC AGCAGCTTCG TGACTCCGAG GAGCGCGCTG 2951
CGGAGCTGGC GAGCCAGCTG GAGTCCACTA CTGCTGCGAA GATGTCAGCG 3001
GAGCAGGACC GCGAGAGCAC GAGGGCCACG CTAGAGCAGC AGCTTCGCGA 3051
ATCCGAGGAG CGCGCTGCGG AGCTGGCGAG CCAGCTGGAG TCCACTACTG 3101
CTGCGAAGAT GTCAGCGGAG CAGGACCGCG AGAGCACGAG GGCCACGCTA 3151
GAGCAGCAGC TTCGTGACTC CGAGGAGCGC GCTGCGGAGC TGGCGAGCCA 3201
GCTGGAGGCC ACTGCTGCTG CGAAGTCGTC GGCGGAGCAG GACCGCGAGA 3251
ACACGAGGGC CGCGTTGGAG CAGCAGCTTC GTGACTCCGA GGAGCGCGCC 3301
GCGGAGCTGG CGAGCCAG 3319
```

( 2 ) INFORMATION FOR SEQ ID NO:3:

( i ) SEQUENCE CHARACTERISTICS:

-continued ( A ) LENGTH: 39 amino acids
( B ) TYPE: amino acid
( D ) TOPOLOGY: linear ( i i ) MOLECULE TYPE: protein ( i x ) FEATURE:
( A ) NAME/KEY: Xaa at position 7 is Asp or Glu, at position 10

( x i ) SEQUENCE DESCRIPTION: SEQ ID NO: 3:

```
Leu Glu Gln Gln Leu Arg Xaa Ser Glu Xaa Arg Ala Ala Glu Leu
1               5                   10                  15

Ala Ser Gln Leu Glu Xaa Thr Xaa Ala Ala Lys Xaa Ser Ala Glu
                20                  25                  30

Gln Asp Arg Glu Xaa Thr Arg Ala Xaa
                35
```